US00PP37049P2

(12) United States Plant Patent
van Swieten

(10) Patent No.: US PP37,049 P2
(45) Date of Patent: Oct. 21, 2025

(54) ***PHALAENOPSIS* PLANT NAMED 'PHA895502'**

(50) Latin Name: *Phalaenopsis hybrida*
Varietal Denomination: PHA895502

(71) Applicant: ANTHURA B.V., Bleiswijk (NL)

(72) Inventor: Martinus Nicolaas Gerardus van Swieten, Utrecht (NL)

(73) Assignee: ANTHURA B.V., Bleiswijk (NL)

( * ) Notice: Subject to any disclaimer, the term of this patent is extended or adjusted under 35 U.S.C. 154(b) by 0 days.

(21) Appl. No.: 19/022,042

(22) Filed: Jan. 15, 2025

(51) Int. Cl.
*A01H 5/02* (2018.01)
*A01H 6/62* (2018.01)

(52) U.S. Cl.
USPC ..... Plt./311

(58) Field of Classification Search
USPC ..... Plt./311
See application file for complete search history.

*Primary Examiner* — Susan McCormick Ewoldt
(74) *Attorney, Agent, or Firm* — C. Anne Whealy

(57) ABSTRACT

A new and distinct cultivar of *Phalaenopsis* plant named 'PHA895502', characterized by its upright and relatively compact plant habit; relatively moderately vigorous growth habit and moderate growth rate; strong flowering stems; healthy and sturdy leaves; freely flowering habit with typically two inflorescences developing per plant, each inflorescence with numerous flowers; purplish pink-colored flowers with white-colored centers and mostly reddish purple-colored labella; and good postproduction longevity.

2 Drawing Sheets

Figure 1:
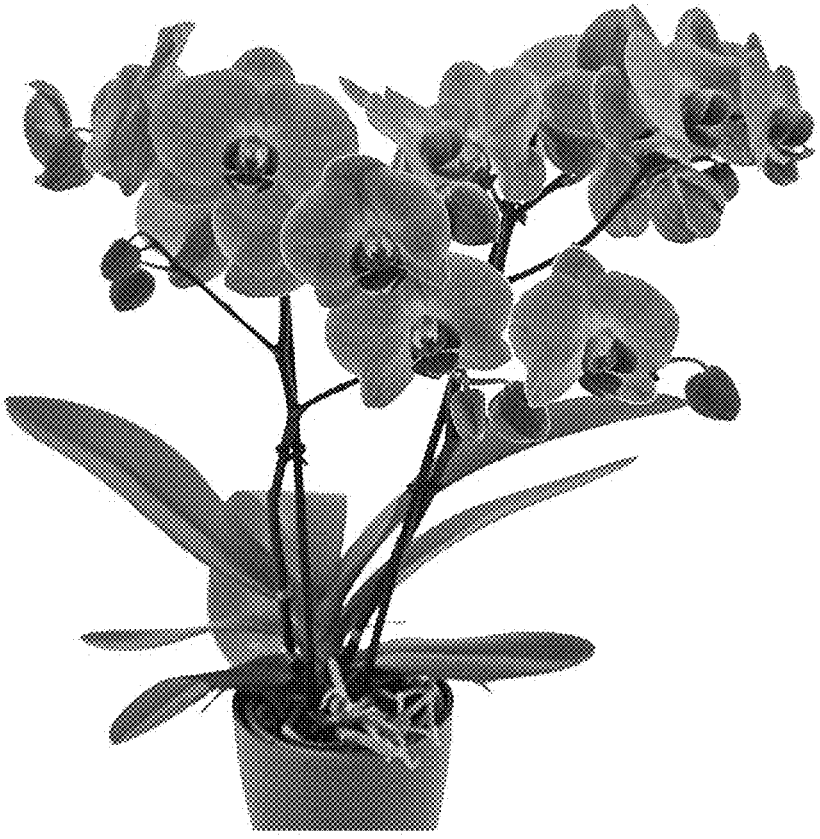

Botanical designation: *Phalaenopsis hybrida.*
Cultivar denomination: 'PHA895502'.

STATEMENT REGARDING PRIOR DISCLOSURES BY INVENTOR and APPLICANT/ASSIGNEE:

A European Community Plant Breeder's Rights application for the instant plant was filed by the Applicant/Assignee of the instant application, Anthura B.V. of Bleiswijk, The Netherlands on Aug. 14, 2024, application number 2024/1890, and published on Oct. 15, 2024. Foreign priority is not claimed to this application.

BACKGROUND OF THE INVENTION

The present invention relates to a new and distinct cultivar of *Phalaenopsis* plant, botanically known as *Phalaenopsis hybrida,* commonly referred to as a *Phalaenopsis* or Moth Orchid and hereinafter referred to by the name 'PHA895502'.

The new *Phalaenopsis* plant is a product of a planned breeding program conducted by the Inventor in Bleiswijk, The Netherlands. The objective of the breeding program is to develop new compact and freely flowering *Phalaenopsis* plants with flowers with unique and attractive patterns and coloration.

The new *Phalaenopsis* plant originated from a cross-pollination in July 2017 in Bleiswijk, The Netherlands of *Phalaenopsis hybrida* 'PHALARALS', disclosed in U.S. Plant Pat. No. 33,097, as the female, or seed, parent with a proprietary selection of *Phalaenopsis hybrida* identified as code number 15-057327-0001, not patented, as the male, or pollen, parent. The new *Phalaenopsis* plant was discovered and selected by the Inventor as a single flowering plant from within the progeny of the stated cross-pollination grown in a controlled greenhouse environment in Bleiswijk, The Netherlands in April 2020.

Asexual reproduction of the new *Phalaenopsis* plant by in vitro meristem propagation in a controlled environment in Bleiswijk, The Netherlands since April 2020 has shown that the unique features of this new *Phalaenopsis* plant are stable and reproduced true to type in successive generations.

SUMMARY OF THE INVENTION

Plants of the new *Phalaenopsis* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'PHA895502'. These characteristics in combination distinguish 'PHA895502' as a new and distinct *Phalaenopsis* plant:

1. Upright and relatively compact plant habit.
2. Relatively moderately vigorous growth habit and moderate growth rate.
3. Strong flowering stems.
4. Healthy and sturdy leaves.
5. Freely flowering habit with typically two inflorescences developing per plant, each inflorescence with numerous flowers.
6. Purplish pink-colored flowers with white-colored centers and mostly reddish purple-colored labella.
7. Good postproduction longevity.

Plants of the new *Phalaenopsis* can be compared to plants of the female parent, 'PHALARALS'. Plants of the new *Phalaenopsis* differ primarily from plants of 'PHALARALS' in the following characteristics:

1. Flowers of plants of the new *Phalaenopsis* are not as broad as flowers of plants of 'PHALARALS'.
2. The labella lateral lobes of plants of the new *Phalaenopsis* are more inwardly curved than the labella lateral lobes of plants of 'PHALARALS'.
3. Petals and sepals of the new *Phalaenopsis* are purplish pink in color with white-colored centers whereas petals and sepals of plants of 'PHALARALS' are light reddish purple in color with white-colored centers.

Plants of the new *Phalaenopsis* can be compared to plants of the male parent selection. Plants of the new *Phalaenopsis* differ primarily from plants of the male parent selection in the following characteristics:

1. Petals of plants of the new *Phalaenopsis* are broadest proximally whereas petals of plants of the male parent selection are broadest at the center.
2. The cirrhose tips of the labella of plants of the new *Phalaenopsis* are longer than the cirrhose tips of the labella of plants of the male parent selection.
3. The central lobe of the labella of plants of the new *Phalaenopsis* is deltoid in shape whereas the central lobe of the labella of plants of the male parent selection is ovate in shape.

Plants of the new *Phalaenopsis* can be compared to plants of *Phalaenopsis hybrida* 'PHA209868', not patented. In side-by-side comparisons, plants of the new *Phalaenopsis* differ primarily from plants of 'PHA209868' in the following characteristics:

1. Flowers of plants of the new *Phalaenopsis* are broader than flowers of plants of 'PHA209868'.
2. The column of flowers of plants of the new *Phalaenopsis* is white and purplish pink in color whereas the column of plants of the 'PHA209868' is solid white in color.

BRIEF DESCRIPTION OF THE PHOTOGRAPHS

The accompanying photographs illustrate the overall appearance of the new *Phalaenopsis* plant showing the colors as true as it is reasonably possible to obtain in colored reproductions of this type. Colors in the photographs may differ slightly from the color values cited in the detailed botanical description which accurately describe the colors of the new *Phalaenopsis* plant.

The photograph on the first sheet (FIG. 1) is a side perspective view of a typical flowering plant of 'PHA895502' grown in a container.

Figure 2:
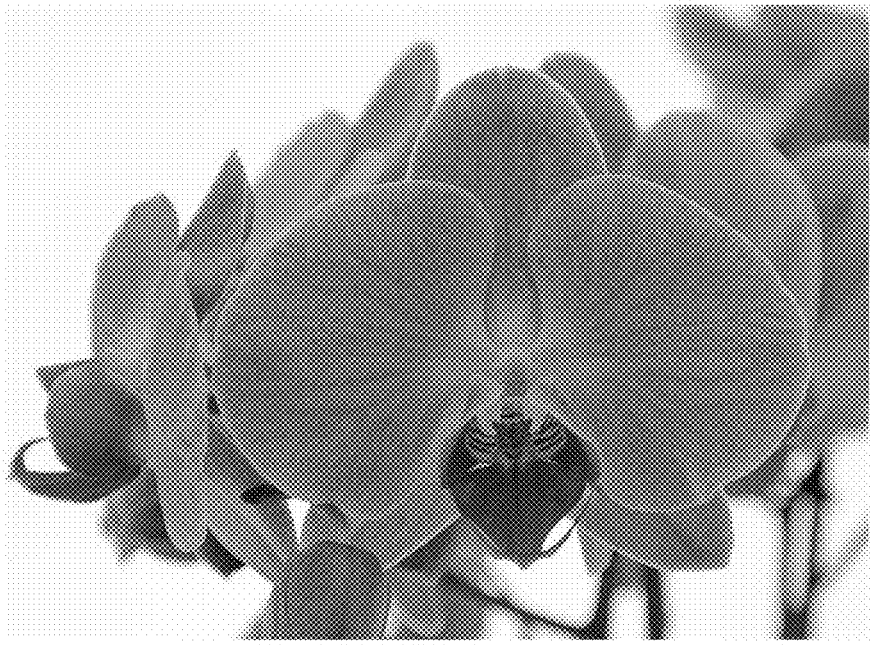

The photograph on the second sheet (FIG. 2) is a close-up view of a typical flowering stem of 'PHA895502'.

DETAILED BOTANICAL DESCRIPTION

The aforementioned photographs and following observations and measurements describe plants grown during the autumn in 9-cm containers in a glass-covered greenhouse in Bleiswijk, The Netherlands and grown under cultural practices typically used in commercial *Phalaenopsis* production. Plants were 16 months old when the photographs and description were taken. During the first 13 months of production of the plants, day and night temperatures averaged 28.5° C., and during the last three months of production of the plants, day and night temperatures averaged 20° C. Throughout the production of the plants, light levels ranged from 100μmol to 180μmol. In the following description, color references are made to The Royal Horticultural Society Colour Chart, 2015 Edition, except where general terms of ordinary dictionary significance are used.

Botanical classification: *Phalaenopsis hybrida* 'PHA895502'.

Parentage:

*Female, or seed, parent.*—*Phalaenopsis hybrida* 'PHALARALS', disclosed in U.S. Plant Pat. No. 33,097.

*Male, or pollen, parent.*—Proprietary selection of *Phalaenopsis hybrida* identified as code number 13-057327-0001, not patented.

Propagation:

*Type.*—By in vitro meristem propagation.

*Time to initiate roots, summer and winter.*—About two weeks at temperatures about 28° C. to 30° C.

*Time to produce a rooted young plant, summer and winter.*—About 20 to 25 weeks at temperatures about 28° C. to 30° C.

*Root description.*—Thick, fibrous; typically light green in color; actual color of the roots is dependent on substrate composition, water quality, fertilizer, substrate temperature and age of roots.

*Rooting habit.*—Freely branching; medium density.

Plant description:

*Plant form and growth habit.*—Herbaceous epiphyte; upright and relatively compact plant habit with typically two inflorescences developing per plant, each inflorescence with numerous flowers; monopodial; relatively moderately vigorous growth habit and moderate growth rate.

*Plant height, substrate level to top of foliar plane.*—About 14 cm.

*Plant height, substrate level to top of floral plane.*—About 31.9 cm.

*Plant diameter or spread.*—About 29.4 cm.

Leaf description:

*Arrangement and quantity.*—Distichous, simple; sessile; about four to seven fully-developed leaves per plant.

*Length.*—About 18.8 cm.

*Width.*—About 6 cm.

*Aspect.*—Semi-erect to slightly curled downward.

*Shape.*—Oblong to narrowly elliptic-oblong; slightly carinate.

*Apex.*—Unequal and narrowly obtuse.

*Base.*—Sheathing. Sheath length: About 2 cm. Sheath width: About 1.3 cm. Sheath color: Close to 143B; towards the apical margin, slightly flushed with close to 147B.

*Margin.*—Entire; not undulate.

*Texture and luster, upper surface.*—Smooth, glabrous; moderately glossy.

*Texture and luster, lower surface.*—Smooth, glabrous; moderately glossy to glossy.

*Venation pattern.*—Camptodromous.

*Color.*—Developing leaves, upper surface: Close to NN137B; narrow marginal edges, close to N200B. Developing leaves, lower surface: Close to 146A and 146B; narrow marginal edges, close to N200A. Fully expanded leaves, upper surface: Close to a blend of 137A and NN137B; venation, close to 147A. Fully expanded leaves, lower surface: Close to 146B; towards the margins and apex, close to 146A; narrow marginal edges, close to N200A and N200B; venation, close to a blend of 144A and 144B.

Inflorescence description:

*Appearance and flowering habit*.—Showy zygomorphic flowers arranged on axillary simple or branched racemes; typically two inflorescences develop per plant; each inflorescence with about twelve flowers; flowers face outwardly on upright to outwardly arching inflorescences supported by upright peduncles; flowers with three petals, two lateral petals and one center petal transformed into a labellum and three sepals.

*Fragrance*.—None detected.

*Time to flower*.—Plants begin flowering about four months after planting; plants flower naturally during the winter into the spring.

*Flower longevity*.—Long flowering period, individual inflorescences maintain good substance for about nine weeks on the plant; flowers not persistent.

*Inflorescence length* (*lowermost flower to inflorescence apex*).—About 17.8 cm.

*Inflorescence width*.—About 20 cm.

*Flower buds*.—Height: About 1.9 cm. Diameter: About 1.2 cm by 1.6 cm. Shape: Broadly ovate. Color: Close to 186A with fine marbling, close to 186C; venation, close to 70A.

*Flower size*.—About 7.5 cm (vertical) by 8.4 cm (horizontal).

*Flower depth*.—About 3 cm.

*Petals, quantity and arrangement*.—Three, two lateral petals and one center petal transformed into a labellum.

*Lateral petals*.—Length: About 3.9 cm. Width: About 5 cm. Shape: Broadly reniform to close to lunate. Apex: Obtuse. Margin: Entire; not undulate. Texture and luster, upper and lower surfaces: Smooth, glabrous, moderately velvety; matte. Color: When opening, upper surface: Close to a blend of N78C and NN78D; towards the apical margin, close to N78D; towards the base, close to NN155A. When opening, lower surface: Close to N78C; center, close to N75D; towards the base, close to N78B. Fully opened, upper surface: Close to N78C; towards the apex and margins, close to N78D; towards the base, close to N155B and at the base, close to N155A; venation, close to NN78D; color does not change with subsequent development. Fully opened, lower surface: Close to a blend of N78C and N78D; center, close to 76A; towards the base, close to N78B and at the base, close to N155A; venation, close to NN78D; color does not change with subsequent development.

*Labella*.—Appearance: Three-parted with two lateral lobes and a central lobe; overall shape, broadly cordate. Length, lateral lobes: About 2 cm. Width, lateral lobes: About 1.4 cm. Length, central lobe: About 2 cm. Width, central lobe: About 5 mm to 19 mm. Length, cirrhose tips: About 1.2 cm. Shape, lateral lobes: Obovate. Shape, central lobe: Deltoid with an elongated apex. Apex, lateral lobes: Obtuse. Apex, central lobe: Acute with two upwardly and backwardly curled cirrhose tips. Margins, lateral and central lobes: Entire. Texture and luster, lateral and central lobes, upper and lower surfaces: Smooth, glabrous, velvety; matte. Callosities: Located at the base of the labellum and attachment point of the lateral petals; about 3.5 mm in length, about 5 mm in width and about 4 mm in height. Color: When opening, upper surface: Lateral lobes: Close to 61A; towards the apex, close to N78B; at the base, close to 155C slightly blotched with close to 8C. Central lobe: Close to 187D; at the base, close to 155C with radial stripes, close to 185A; cirrhose tips, close to NN74B. Callosities: Close to 11C; distally, close to 17B with dense dots and blotches, close to 185A. When opening, lower surface: Lateral lobes: Close to 187C; towards the apex, close to N78C; at the base, blotched with close to 156D. Central lobe: Close to 183C; at the base, close to 157C; cirrhose tips, close to N78C and N78D. Fully opened, upper surface: Lateral lobes: Close to 61A; towards the apex, close to N78B; at the base, close to 155C slightly blotched with close to 8C. Central lobe: Close to 187D; at the base, close to 155C with radial stripes, close to 185A; cirrhose tips, close to NN74B. Callosities: Close to 12C; distally, close to 17A with dense dots and blotches, close to 185A. Fully opened, lower surface: Lateral lobes: Close to 187C; towards the apex, close to N78C; at the base, blotched with close to 156D. Central lobe: Close to 183C; at the base, close to 157C; cirrhose tips, close to N78C and N78D.

*Sepals*.—Quantity and arrangement: Three, one upper dorsal sepal and two lower lateral sepals. Length, dorsal sepal: About 4.1 cm. Width, dorsal sepal: About 3 cm. Length, lateral sepals: About 4.2 cm. Width, lateral sepals: About 2.5 cm. Shape, dorsal sepal: Broadly elliptic. Shape, lateral sepals: Ovate. Apex, dorsal sepal: Minutely retuse. Apex, lateral sepals: Bluntly acute. Base, dorsal and lateral sepals: Cuneate. Margins, dorsal and lateral sepals: Entire; not undulate. Texture and luster, dorsal and lateral sepals, upper and lower surfaces: Smooth, glabrous, moderately velvety; matte. Color, dorsal sepal: When opening, upper surface: Close to N78C; center, close to N78D. When opening, lower surface: Close to N78C; center, close to N77D. Fully opened, upper surface: Close to N78C and N78D; center, close to N75B; narrow marginal edges, close to 76D; venation, close to N78B. Fully opened, lower surface: Close to a blend of N78B and NN78D; distally, close to N78C and 72C; venation, close to NN78C. Color, lateral sepals: When opening, upper surface: Close to N75A; towards the base, close to 150D. When opening, lower surface: Close to N78B; towards the base, close to 154D; venation, close to 71A. Fully opened, upper surface: Close to N78C and N78D; center, close to 76B; at the base, close to 157A; venation, similar to lamina color. Fully opened, lower surface: Close to N78B and N78C; venation, close to N78B.

*Peduncles*.—Length: About 30.4 cm. Diameter: About 4 mm. Strength: Strong. Aspect: Upright to outwardly arching. Texture and luster: Smooth, glabrous; matte. Color: Close to N200A densely covered with fine dots and fine marbling, close to 147C and 147D.

*Pedicels*.—Length: About 3 cm. Diameter: About 2 mm. Strength: Moderately strong. Aspect: About 50° from peduncle axis. Texture and luster: Smooth, glabrous; matte. Color: Close to 147D; distal end, close to 75C; proximal end, close to 147B.

*Reproductive organs*.—Androecium: Column length: About 8 mm. Column width: About 5 mm. Column color: Close to N78C and towards the base, close to NN155D. Pollinia quantity: Two. Pollinia diameter (per two pollinia): About 2 mm. Pollinia color: Close to 23A. Gynoecium: Stigma length: About 3.5 mm. Stigma width: About 4.5 mm. Stigma shape: Reniform. Stigma color: Close to N155A. Ovary length: About 7 mm. Ovary diameter: About 1 mm. Ovary color: Close to 150D. Seeds and fruits: To date, seed and fruit development have not been observed on plants of the new *Phalaenopsis*.

Pathogen & pest resistance: To date, plants of the new *Phalaenopsis* have not been shown to be resistant to pathogens and pests common to *Phalaenopsis* plants.

Temperature tolerance: Plants of the new *Phalaenopsis* have been observed to tolerate high temperatures about 40° C. and are suitable for USDA Hardiness Zones 10 to 12.

It is claimed:

1. A new and distinct *Phalaenopsis* plant named 'PHA895502' as herein illustrated and described.

* * * * *